US00PP25935P3

(12) United States Plant Patent
Bunnik

(10) Patent No.: US PP25,935 P3
(45) Date of Patent: Sep. 22, 2015

(54) ***GUZMANIA* PLANT NAMED 'BUNDEWH'**

(50) Latin Name: ***Guzmania* hybrid**
Varietal Denomination: BUNDEWH

(71) Applicant: Bjorn Bunnik, Kudelstaart (NL)

(72) Inventor: Bjorn Bunnik, Kudelstaart (NL)

(73) Assignee: 3B Fundus B.V (NL)

( * ) Notice: Subject to any disclaimer, the term of this patent is extended or adjusted under 35 U.S.C. 154(b) by 162 days.

(21) Appl. No.: 13/998,393

(22) Filed: Oct. 28, 2013

(65) Prior Publication Data

US 2015/0121593 P1 Apr. 30, 2015

(51) Int. Cl.
*A01H 5/12* (2006.01)

(52) U.S. Cl.
USPC ..... Plt./371

(58) Field of Classification Search
USPC ..... Plt./371
See application file for complete search history.

*Primary Examiner* — Anne Grunberg
(74) *Attorney, Agent, or Firm* — Cassandra Bright

(57) ABSTRACT

A new and distinct *Guzmania* cultivar named 'BUNDEWH' is disclosed, characterized by unique white inflorescence color and compact plant habit. The new variety is a *Guzmania*, typically produced as an indoor ornamental plant.

1 Drawing Sheet

Latin name of the genus and species: *Guzmania* hybrid.
Variety denomination: 'BUNDEWH'.

BACKGROUND OF THE INVENTION

This application relates to a new cultivar of *Guzmania*. The new variety is the product of chance discovery, by the inventor, Bjorn Bunnik. The new variety originated as a naturally occurring whole plant mutation from the unpatented commercial variety *Guzmania* 'Voila'.

The new variety was first selected by the inventor, in at a commercial greenhouse in Kudelstaart, the Netherlands. After identifying the new variety as a potentially interesting selection, the inventor continued confidential testing and propagation of 'BUNDEWH', assessing stability of the unique characteristics of this variety.

Asexual reproduction of the new cultivar 'BUNDEWH' was first performed at a commercial laboratory in Kudelstaart, Netherlands by tissue culture in 2008. Access to all plants was restricted, as plants were kept in a greenhouse not open to the public. Through subsequent propagation, multiple generations have been reproduced, which have shown that the unique features of this cultivar are stable and reproduced true to type.

SUMMARY OF THE INVENTION

The cultivar 'BUNDEWH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BUNDEWH'. These characteristics in combination distinguish 'BUNDEWH' as a new and distinct *Guzmania* cultivar:

1. White inflorescence.
2. Green leaves.
3. Compact plant shape.

PARENT COMPARISON

Plants of the new cultivar 'BUNDEWH' are similar to the parent in most horticultural characteristics. However the new variety, 'BUNDEWH' differs from the 'Voila' in the following characteristics:

1. New variety is a more compact plant.
2. Inflorescence of 'Voila' is pink.

COMMERCIAL COMPARISON

'BUNDEWH' is similar in most horticultural characteristics to the patented commercial variety *Guzmania* 'Bolero' U.S. Plant Pat. No. 11,893 in most horticultural characteristics. However the new variety, 'BUNDEWH' differs from 'Bolero' in the following characteristics:

1. Inflorescence of 'BUNDEWH' is shorter.
2. Leaves of the new variety are shorter and broader.
3. Plant habit of the new variety is more compact.

BRIEF DESCRIPTION OF THE PHOTOGRAPH

The accompanying photograph in FIG. 1 illustrates in full color a typical plant of 'BUNDEWH' grown in a commercial greenhouse in De Kwakel, Netherlands. The plant is 20 months old from a rooted cutting, in a 12 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a typical plant of 'BUNDEWH' grown in a commercial greenhouse in De Kwakel, Netherlands. The plant is 20 months old from a rooted cutting, in a 12 cm pot. Temperatures ranged between 20° C. and 28° C. during the day 18° C. and 22° C. at night. No supplemental lighting was given. Measurements and numerical values represent averages of typical plant types.

Botanical classification: *Guzmania* hybrid 'BUNDEWH'.

PROPAGATION

Type of propagation typically used: Tissue culture.

Time to initiate roots: About 15 days at approximately 20° C.

Time to produce a rooted cutting/liner: About 180 days at approximately 22° C.

Root description: Moderately dense, moderately branched, fine, fibrous, not fleshy, coloured brown; near RHS 200A to 200D.

PLANT

Growth habit: Upright, monopodial.

Height: Average: 34.5 cm.

Plant spread: Average: 58.0 cm.

Normal pot size: 12 cm (circular).

Growth rate: Moderate.

Branching characteristics: Monopodial, leaves form a basal rosette, inflorescence grows from the center of the rosette.

Number of leaves per scape: Average: 24.

Stem length: No stems present, scape grows directly from rosette.

FOLIAGE

Leaf:

*Arrangement*.—Rosulate; leaves (average: 24) placed in a basal rosette.

*Average length*.—Approximately 30.2 cm.

*Average width*.—Approximately 4.1 cm (measured at 50% length of the leaf blade).

*Shape of blade*.—Ligulate.

*Aspect*.—Base in an average angle of 40° to horizontal, tip arching downward in an average angle of 40° to horizontal.

*Apex*.—Apiculate, curved downward in an average angle of 40° to horizontal.

*Base*.—Sheathing. Sheath length: Average 7.3 cm. Sheath width: Average 8.4 cm. Sheath color: Greyed-yellow, near RHS 166A.

*Margin*.—Entire.

*Texture of top surface*.—Glabrous, glossy.

*Texture of bottom surface*.—Glabrous, glossy.

*Color*.—Young foliage upper side: Green to yellow-green; in between RHS 143A and 146A. Young foliage under side: Yellow-green; in between RHS 144A and 146B. Mature foliage upper side: Green to yellow-green; in between.

*Width*.—Approximately 2.9 cm (measured at 50% of the leaf blade).

*Quantity*.—Average 15.

*Tip*.—Apiculate to long apiculate.

*Base*.—Sheathing. Sheath length: Approximately 2.4 cm. Sheath width: Approximately 4.4 cm. Sheath color: Yellow-green; near RHS 145B.

*Margin*.—Entire.

*Coloration terminal bracts*.—Upper side: Yellow-green and greyed-yellow; near RHS 150D and 160D, top of lower terminal brachts yellow-green; near RHS 144A. Under side: Yellow-green and greyed-yellow; near RHS 150D and 160D, top of lower terminal brachts yellow-green; near RHS 144A.

FLOWER

Individual Flowers not observed.

REPRODUCTIVE ORGANS

Not observed.

OTHER CHARACTERISTICS

Disease resistance: Neither resistance nor susceptibility to the normal diseases and pests of *Guzmania* has been observed.

Temperature tolerance: Observed to tolerate temperatures to 35° C. without any negative effects. Temperature tolerance above this range has not been observed. Tolerance of cold temperatures has not been observed.

Fruit/seed production: No fruits/seeds detected to date.

What is claimed is:

1. A new and distinct cultivar of *Guzmania* plant named 'BUNDEWH' as herein illustrated and described.

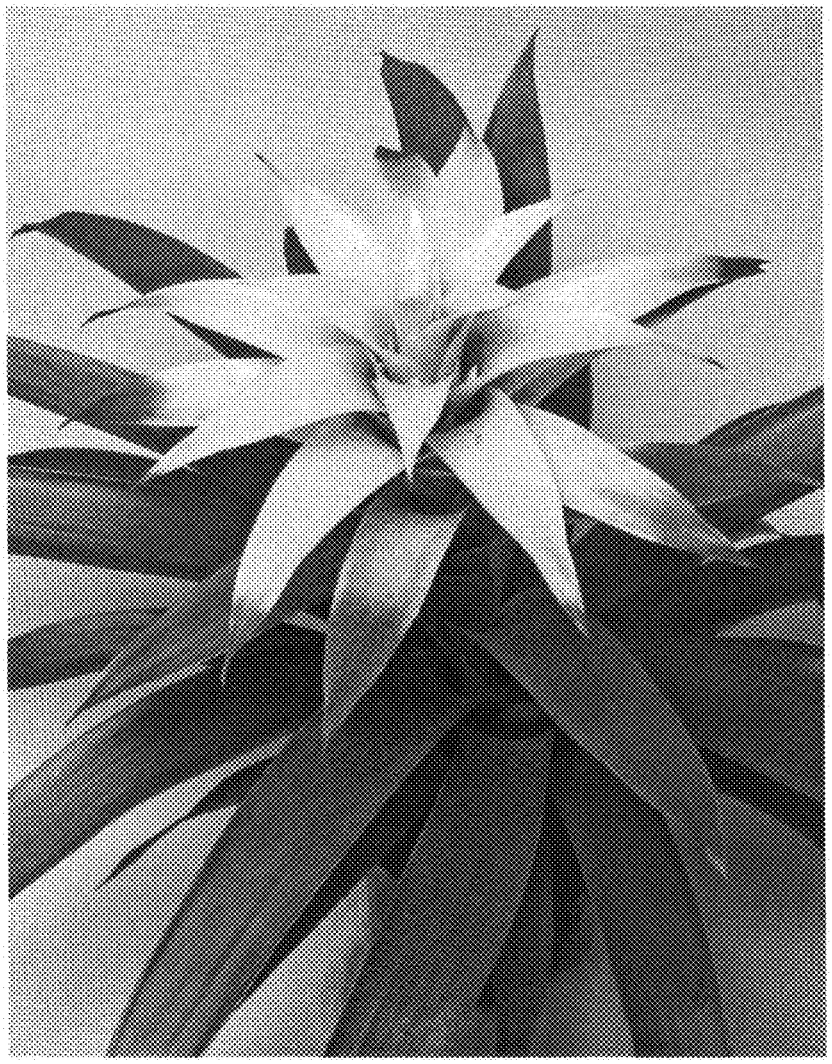

* * * * *